(12) United States Patent
Stopp et al.

(10) Patent No.: US 11,062,465 B2
(45) Date of Patent: Jul. 13, 2021

(54) OPTICAL TRACKING

(71) Applicant: Brainlab AG, Munich (DE)

(72) Inventors: Sebastian Stopp, Munich (DE); Johannes Manus, Munich (DE); Sven Flossmann, Feldkirchen (DE); Martin Pregler, Assling (DE); Uli Mezger, Heimstetten (DE); Manfred Weiser, Munich (DE)

(73) Assignee: BRAINLAB AG, Munich (DE)

( * ) Notice: Subject to any disclaimer, the term of this patent is extended or adjusted under 35 U.S.C. 154(b) by 111 days.

(21) Appl. No.: 16/083,928

(22) PCT Filed: Mar. 9, 2017

(86) PCT No.: PCT/EP2017/055584
§ 371 (c)(1),
(2) Date: Sep. 11, 2018

(87) PCT Pub. No.: WO2017/157763
PCT Pub. Date: Sep. 21, 2017

(65) Prior Publication Data
US 2020/0193622 A1    Jun. 18, 2020

(30) Foreign Application Priority Data

Mar. 17, 2016 (WO) .................. PCT/EP2016/055816

(51) Int. Cl.
*G06T 7/292* (2017.01)
*A61B 34/20* (2016.01)
(Continued)

(52) U.S. Cl.
CPC .............. *G06T 7/292* (2017.01); *A61B 34/20* (2016.02); *G06T 7/70* (2017.01); *A61B 90/20* (2016.02);
(Continued)

(58) Field of Classification Search
CPC ............ A61B 2034/2055; A61B 34/20; A61B 2090/3983; A61B 2034/2068;
(Continued)

(56) References Cited

U.S. PATENT DOCUMENTS 6,384,908 B1    5/2002   Schmidt et al.
6,434,416 B1    8/2002   Masakazu et al.
(Continued)

FOREIGN PATENT DOCUMENTS

DE    102014102425 A1    8/2015
EP         2769689 A1    8/2014
WO      2015024600 A1    2/2015

OTHER PUBLICATIONS

Doignon et al., Pose Estimation and Features Tracking for Robot Assisted Surgery with Medical Imaging, Chapter 1 of Book titled: Unifying Perspectives in Computational and Robot Vision, 2007—pp. 1-23, France www.irisa.fr/lagadic/pdf/2007_chapter_doignon. pdf.
(Continued)

*Primary Examiner* — Obafemi O Sosanya
(74) *Attorney, Agent, or Firm* — Tucker Ellis LLP

(57) ABSTRACT

A medical tracking method for tracking a spatial position of a medical instrument within a medical workspace including an anatomical structure of a patient. The method includes: acquiring, using a first camera targeted on the medical workspace, instrument position data describing a spatial position of the medical instrument with respect to a first camera; acquiring, using a second camera and at least one optical tracking marker that is adapted to be recognized by the second camera, camera position data describing a spatial position of the first camera with respect to the anatomical structure, determining, based on the instrument position data and the camera position data, tracking data describing the spatial position of the medical instrument with respect to the
(Continued)

anatomical structure; and tracking the spatial position of the medical instrument within the medical workspace using the tracking data.

19 Claims, 10 Drawing Sheets

(51) Int. Cl.
*G06T 7/70* (2017.01)
*A61B 90/20* (2016.01)
*A61B 90/00* (2016.01)

(52) U.S. Cl.
CPC ..... *A61B 90/361* (2016.02); *A61B 2034/2057* (2016.02); *A61B 2034/2065* (2016.02); *A61B 2090/363* (2016.02); *A61B 2090/364* (2016.02); *A61B 2090/371* (2016.02); *A61B 2090/3937* (2016.02); *A61B 2090/3983* (2016.02); *G06T 2207/30204* (2013.01)

(58) Field of Classification Search
CPC ....... A61B 90/361; A61B 90/37; A61B 90/39; A61B 2090/3937; A61B 2017/00464; A61B 5/064; A61B 34/2057; A61B 90/20; A61B 2090/367
See application file for complete search history.

(56) References Cited

U.S. PATENT DOCUMENTS

| | | | |
|---|---|---|---|
| 6,671,058 B1 | 12/2003 | Braunecker et al. | |
| 7,912,532 B2 | 3/2011 | Schmidt et al. | |
| 8,059,267 B2 | 11/2011 | Armstrong | |
| 8,320,612 B2 | 11/2012 | Knobel et al. | |
| 8,625,107 B2 | 1/2014 | Kusik et al. | |
| 8,657,809 B2 | 2/2014 | Schoepp | |
| 8,880,151 B1 | 11/2014 | Stolka et al. | |
| 2006/0281971 A1* | 12/2006 | Sauer | A61B 34/20 600/109 |
| 2017/0119493 A1* | 5/2017 | Bailey | H04N 5/23203 |

OTHER PUBLICATIONS

European Patent Office, International Search Report and Written Opinion, corresponding to PCT/EP2017/055584, dated Jul. 13, 2017, pp. 1-13.

\* cited by examiner

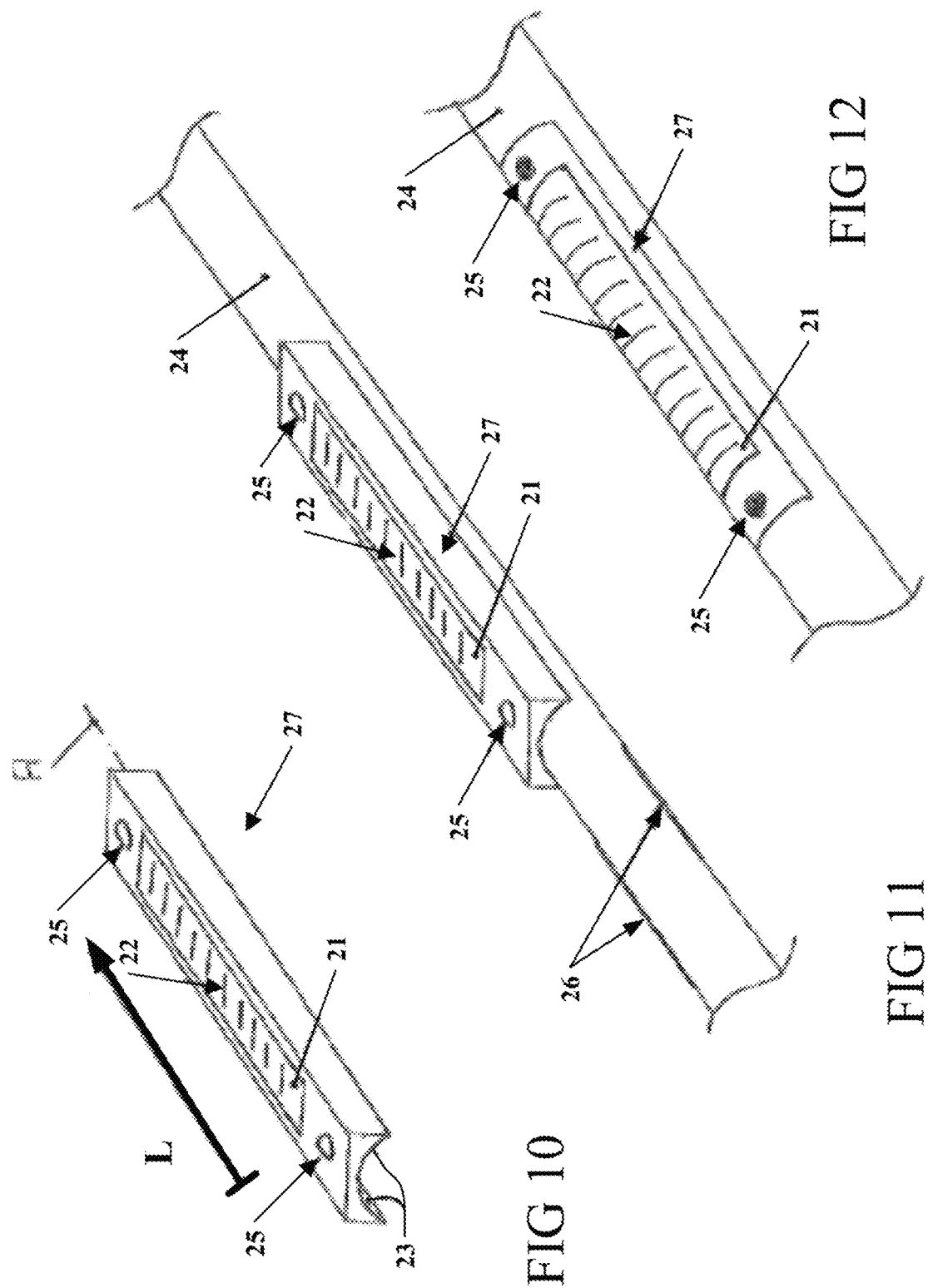

OPTICAL TRACKING

RELATED APPLICATION DATA

This application is a national phase of International Application No. PCT/EP2017/055584 filed Mar. 9, 2017 and published in the English language. International Application No. PCT/EP2017/055584 claims priority to International Application No. PCT/EP2017/055816 filed Mar. 16, 2016.

In the following, the present invention is discussed within the frame work of five parts (part I, part II, part III, part IV and part V), the specific technical contents of which may be combined wherever this is technically expedient and/or feasible. Specifically, a feature of one embodiment discussed in one part, which adds an additional function to another embodiment discussed in another part can for example be added to said other embodiment of said other part. However, the technical content discussed in parts I to V may also be considered as an independent invention.

Part I: Microscope Video Tracking

The present part of the invention relates to a computer program for tracking a spatial position of at least one medical instrument within a medical workspace, a corresponding non-transitory program storage medium storing such a program and a computer for executing the program as well as a corresponding tracking system determining the spatial position of at least one medical instrument within a medical workspace.

Part II: Instrument Ring Marker with Contour

The present part of invention relates to a medical instrument having a body section and at least three tracking markers which run circumferentially around different parts of the body section, wherein the cross-sectional areas of these different parts have a different size.

Part III: Attachable Marker Sticker

The present part of the invention relates to a medical tracking marker being adapted to be recognized by an optical tracking system that comprises a section that produces an orientation dependent optical pattern. The present invention further relates to a corresponding computer program for tracking an object being fitted with such tracking marker, a non-transitory computer-readable storage medium storing such computer program and a computer for executing the program.

Part IV: Gray Scale Marker Tracking

The present part of the invention relates to a medical tracking marker having a recognition section that produces an orientation dependent optical pattern, a corresponding computer program, a non-transitory program storage medium storing such a program and a computer for executing the program.

Part V: Ring Marker Codification

The present part of the invention relates to a computer program for identifying a medical device within a medical workspace, a corresponding non-transitory program storage medium storing such a program and a computer for executing the program as well as a corresponding medical device being identified and tracked by performing such computer program, and a corresponding medical tracking system for identifying a medical device within a medical workspace.

BACKGROUND

Part I: Microscope Video Tracking

Known tracking systems that utilize an optical video camera for tracking purposes are known, for example from U.S. Pat. No. 8,657,809. This system comprises a camera which is mounted to the head of a patient. In order for the camera to track a surgical tool above the patient, the line of sight between the camera and the tool must not be interrupted.

The present invention allows for a more reliable approach to track a medical instrument within a medical workspace via a video camera, which even allows for a registration of an image dataset.

Aspects of the present invention, examples and exemplary steps and their embodiments are disclosed in the following. Different exemplary features of the invention can be combined in accordance with the invention wherever technically expedient and feasible.

Part II: Instrument Ring Marker with Contour

U.S. Pat. No. 8,880,151 discloses a longitudinal instrument having a ring-pattern that can be recognized by a camera which is mounted on an ultrasound device. The spatial position of the instrument is determined based on the coded information that can be obtained from the ring pattern.

The present invention provides a more reliable and more accurate determination of a spatial position of such an instrument by means of an optical tracking system which may have one single video camera.

Aspects of the present invention, examples and their embodiments are disclosed in the following. Different exemplary features of the invention can be combined in accordance with the invention wherever technically expedient and feasible.

Part III: Attachable Marker Sticker

In the technical field of medical tracking systems and medical tracking methods, a large variety of approaches to track objects in three-dimensional space are known. For example, some systems comprise a stereoscopic camera array which allows to determine the spatial position (i.e. the spatial location and/or the spatial orientation) very precisely within six dimensions/degrees of freedom. However, such systems require large and cumbersome tracking markers attached to the respective objects. A different type of tracking systems comprise a monocular camera that provide a single video image from which at least some of the information as to the spatial orientation of objects seen on the image can be derived by computer vision algorithms including edge detection (for example, by methods according to LaPlace, to Canny, or to Sobel, Hough transformation, line segment detection etc.) However, this approach often does not provide all the information needed for tracking an object within a medical workspace. Further, medical tracking markers are known, which provide a plurality of orientation-dependent patterns, for example from U.S. Pat. No. 8,059,267 or 6,384,908.

The present invention allows for a more convenient and more accurate position detection of objects within a medical workspace.

Aspects of the present invention, examples and exemplary steps and their embodiments are disclosed in the following. Different exemplary features of the invention can be combined in accordance with the invention wherever technically expedient and feasible.

Part IV: Gray Scale Marker Tracking

In the technical field of medical tracking systems and medical tracking methods, a large variety of approaches to track objects in three-dimensional space are known. For example, some systems comprise a stereoscopic camera array which allows to determine the spatial position (i.e. the spatial location and/or the spatial orientation) very precisely within six dimensions/degrees of freedom. However, such systems require large and cumbersome tracking markers attached to the respective objects. A different type of tracking systems comprise a monocular camera that provide a single video image from which at least some of the information as to the spatial orientation of objects seen on the image can be derived by computer vision algorithms including edge detection (for example, by methods according to LaPlace, to Canny, or to Sobel, Hough transformation, line segment detection etc.) However, this approach often does not provide all the information needed for tracking an object within a medical workspace.

The present invention allows for a more convenient and more accurate position detection of objects within a medical workspace.

Aspects of the present invention, examples and exemplary steps and their embodiments are disclosed in the following. Different exemplary features of the invention can be combined in accordance with the invention wherever technically expedient and feasible.

Part V: Ring Marker Codification

Within the technical field of image guided surgery it is desirable to instantaneously know the type and the geometric properties of medical instrument and devices which are tracked by the medical tracking system, without having to perform time-consuming calibration procedures for which an uncalibrated instrument is moved in a predetermined manner with respect to a so-called calibration matrix. In order to avoid such calibration procedures, so-called pre-calibrated instruments are known. For such pre-calibrated instruments, the type and geometric properties are stored in a database on a computer connected to the tracking system and a corresponding navigation system.

Further, each instrument is provided with a specific tracking marker that allows the tracking and/or navigation system to biuniquely assign a specific tracking marker detected by the tracking system with instrument data obtained from the database, which describes the instrument that is provided with this tracking marker. For optical tracking systems, marker arrays comprising a plurality of retro-reflective marker spheres are known, which are disposed in a unique spatial arrangement. In case the unique spatial arrangement is known to the tracking and/or navigation system, the type and the geometric properties, for example the position of the instrument tip with respect to the tracking markers is instantaneously known. However, these marker arrays with marker spheres provided in a biunique spatial arrangement are relatively cumbersome.

The present invention allows for a more desirable approach to identify medical devices within a medical workspace.

Aspects of the present invention, examples and exemplary steps and their embodiments are disclosed in the following. Different exemplary features of the invention can be combined in accordance with the invention wherever technically expedient and feasible.

SUMMARY

Part I: Microscope Video Tracking

In the following, a short description of the specific features of the present invention is given which shall not be understood to limit the invention only to the features or a combination of the features described in this section.

The disclosed tracking method encompasses determining the spatial position of at least one medical instrument within a medical workspace by means of a video camera that forms part of a microscope looking down on a patient lying on a patient couch. In order to determine the instrument's spatial position relative to an anatomical structure, the spatial position of the microscope video camera with respect to the anatomical structure is in turn determined with the help of a further video camera that is either fixed to the anatomical structure or to the microscope, or may even be independently installed within the operating theater. From the determined relative position or relative pose of the instrument and the microscope, and from the determined relative position of the microscope and the anatomical structure, the relative position of the instrument and the anatomical structure is then calculated.

Part II: Instrument Ring Marker with Contour

In the following, a short description of the specific features of the present invention is given which shall not be understood to limit the invention only to the features or a combination of the features described in this section.

The disclosed trackable medical instrument comprises a plurality of ring-shaped and optically recognizable tracking markers, which are arranged at predetermined distances along the longitudinal axis of the instrument. Further, the ring-shaped markers run around different parts of the instrument having a different size, such that the ring-shaped tracking markers also have different diameters. With these different diameters, the orientation of the instrument is easier to determine via at least one optical camera of a medical tracking system.

Part III: Attachable Marker Sticker

In the following, a short description of the specific features of the present invention is given which shall not be understood to limit the invention only to the features or a combination of the features described in this section.

The present invention provides a medical tracking marker and a corresponding tracking method, wherein the tracking marker provides an optical pattern that depends on the orientation of the tracking markers with respect to an optical camera of the tracking system recognizing said marker. A certain predetermined part of the information needed for determining the spatial position of an object fitted with such tracking marker is derived from the orientation dependent optical pattern. The pattern may be actively formed by recognition section which emits electromagnetic radiation (for example light), or passively by a recognition section which reflects and/or transmits electromagnetic radiation (for example light).

Part IV: Gray Scale Marker Tracking

In the following, a short description of the specific features of the present invention is given which shall not be understood to limit the invention only to the features or a combination of the features described in this section.

A disclosed medical tracking marker comprises at least one recognition section that produces at least one orientation dependent optical pattern by having lower areas and higher areas, wherein either the lower or higher areas are optically dark and either the higher or lower areas is optically bright. Seen from a distance, the recognition section will change its appearance depending on the viewing direction on the recognition section, which allows to derive the angular orientation of the tracking marker or an object to which the tracking marker is attached, from the optical appearance of the respective in at least one image obtained from a camera of an optical tracking system.

Part V: Ring Marker Codification

In the following, a short description of the specific features of the present invention is given which shall not be understood to limit the invention only to the features or a combination of the features described in this section.

The disclosed identification method encompasses acquiring data for a tracked medical device having at least two tracking markers, the data describing the number of the markers, the color of at least one marker, the width of at least one marker and/or the spacing between at least two markers, thereby providing a definite description of the corresponding instrument. This acquired data then allows for finding the dataset stored on a database which describes at least the type and/or the geometric properties of this instrument.

BRIEF DESCRIPTION OF THE DRAWINGS

FIG. 10 shows a first embodiment of the disclosed medical tracking marker,

FIG. 11 shows the tracking marker of FIG. 10 attached to an elongated instrument;

FIG. 12 shows a second embodiment of the disclosed medical tracking marker attached to an elongated instrument;

DETAILED DESCRIPTION

Figure 1:
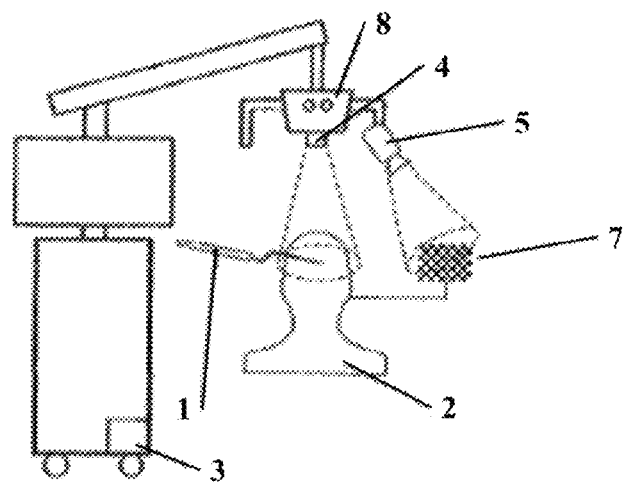
FIG. 1 shows a first embodiment of the disclosed tracking system.

In this section, a description of the general features of the present invention is given for example by referring to possible embodiments of the invention.

In general, the invention reaches the aforementioned object by providing, in a first aspect, a computer-implemented method for tracking a spatial position of at least one medical instrument within a medical workspace. The method comprises executing, on at least one processor of at least one computer, the following exemplary steps which are executed by the at least one processor.

In a (for example first) exemplary step, instrument position data is acquired which describes a spatial position of at least one medical instrument with respect to a first camera by an evaluation of at least one image provided by the at least one first camera, which shows the at least one medical instrument. For this purpose, the at least one instrument may comprise specific tracking markers adapted to be recognized by a video camera. Such specific tracking markers are discussed in Parts II, III and IV and may form part of the invention discussed in Part I, but may also be considered as separate inventions. However, the at least one instrument may also be recognized by optical characteristics such as an identifiable structure or shape. Further, the values for the focus and the zoom of the camera can provide data for determining the spatial position of an instrument and/or anatomical structure with respect to a camera directed to this instrument.

Part I: Microscope Video Tracking
General Description

In a further (for example second) exemplary step, camera position data is acquired which describes a spatial position of the at least one first camera with respect to an anatomical structure. For this purpose, at least one second camera and at least one optical tracking marker recognizable by the at least one second camera is provided. For example, a conventional stereoscopic camera array can be provided together with a conventional tracking marker array comprising one or more retro-reflective marker spheres, just as well as a single video camera together with a trackable marker having a known optical pattern (such as a checkerboard-design) that allows for determining a spatial location and orientation of the marker and any object rigidly connected to that marker.

In a further (for example third) exemplary step, the instrument position data and the camera position data is used to determine tracking data that describes the spatial position of the at least one medical instrument with respect to the anatomical structure.

In a further example, the first camera is rigidly coupled to a medical microscope targeted on the medical workspace, wherein the first camera is in particular a microscope-integrated camera. With the employment of a camera that is assigned a medical microscope that may in particular look down on a patient lying on a patient couch, it is possible to advantageously use of an illumination lamp of the microscope illuminating the workspace and therefore also the anatomical structure and the at least one medical instrument. Since such camera is fixedly attached to the microscope, the position of any object seen by the microscope's camera can be determined within a coordinate system assigned to the microscope.

Further, the first camera may also be freely movable relative to the anatomical structure. For example, a mobile microscope with an integrated video camera could be provided and advantageously arranged at any desired position next to the medical workspace.

At least one second camera is then used for determining the relative position between the first camera and the anatomical structure, which may either be rigidly coupled to the first camera or to the anatomical structure, wherein the corresponding tracking marker to be seen by the at least one second camera is correspondingly coupled in a rigid manner either to the anatomical structure or the first camera. Both, the second camera and the tracking marker to be seen by the second camera may be located away from the medical workspace so that possible interruptions of the line of sight between the camera and the tracking marker can be prevented. In case the second camera is coupled to the anatomical structure, a pivoting mechanism may be provided to allow the second camera to be pivoted between at least two known orientations (i.e. the first orientation with respect to the second orientation is known), one orientation being directed towards the workspace (which allows the camera to detect a medical instrument during a registration procedure) and a second orientation being directed towards the tracking marker coupled to the first camera (which is necessary for determining the relative position between the first camera and the anatomical structure).

In another embodiment the second camera may be an "external" camera that is positioned independently from both, the anatomical structure and the first camera. In this embodiment, it is necessary to provide both, the anatomical structure and the first camera with a tracking marker that can be detected by the external second camera.

The disclosed method may further comprise a (for example fourth) exemplary step of acquiring registration data that describes a spatial correspondence of a pre-acquired dataset of the anatomical structure and the actual anatomical structure within the medical workspace. Such image registration allows for calculating and displaying a virtual representation of the at least one medical instrument in a correct spatial arrangement relative to a two-dimensional or three-dimensional image obtained from a pre-acquired image dataset of the patient showing the anatomical structure. The pre-acquired image dataset may be of any conceivable type and may specifically contain CT-images, MR-images and/or ultrasound images.

As already indicated further above, any of the tracking markers used in the context of the method and apparatus disclosed herein may comprise a two-dimensional optical pattern that can be detected by an optical camera. For example, the optical pattern may provide a checkerboard pattern that may be optically recognized within the visible range of light.

Further, the step of acquiring registration data may involve at least one registration procedure selected form the list containing:
- a landmark registration using a tracked pointer instrument;
- a landmark registration involving focusing the medical microscope on at least one predefined landmark of the anatomical structure;
- a video registration using the medical microscope or a second video camera; scanning the surface of the anatomical structure using a surface scanner or any other suitable registration procedure.

In a second aspect, the invention is directed to a corresponding system for tracking a spatial position of at least one medical instrument within a medical workspace including an anatomical structure of a patient. This system may comprise at least one computer having at least one processor that is adapted to perform any procedural step that has been explained above.

In a third aspect, the invention is directed to a non-transitory computer-readable storage medium storing a computer program which, when executed on at least one processor of at least one computer or loaded into the memory of at least one computer, causes the at least one computer to perform a method that has been described further above.

In a fourth aspect, the invention is directed to at least one computer comprising the non-transitory computer-readable program storage medium according to the third aspect.

It is within the scope of the present invention to combine one or more features of one or more embodiments or aspects of the invention in order to form a new embodiment wherever this is technically expedient and/or feasible.

Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, II-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Service™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer.

Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" c also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The n-dimensional image of a body is registered when the spatial location of each point of an actual object within a space, for example a body part in an operating theatre, is assigned an image data point of an image (CT, MR, etc.) stored in a navigation system.

Image registration is the process of transforming different sets of data into one co-ordinate system. The data can be multiple photographs and/or data from different sensors, different times or different viewpoints. It is used in computer vision, medical imaging and in compiling and analyzing images and data from satellites. Registration is necessary in order to be able to compare or integrate the data obtained from these different measurements.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

The invention also relates to a navigation system for computer-assisted surgery, comprising: the computer of the preceding claim, for processing the absolute point data and the relative point data;
a detection device for detecting the position of the main and auxiliary points in order to generate the absolute point data and to supply the absolute point data to the computer;
a data interface for receiving the relative point data and for supplying the relative point data to the computer; and
a user interface for receiving data from the computer in order to provide information to the user, wherein the received data are generated by the computer on the basis of the results of the processing performed by the computer.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker holder is understood to mean an attaching device for an individual marker which serves to attach the marker to an instrument, a part of the body and/or a holding element of a reference star, wherein it can be attached such that it is stationary and advantageously such that it can be detached. A marker holder can for example be rod-shaped and/or cylindrical. A fastening device (such as for instance a latching mechanism) for the marker device can be provided at the end of the marker holder facing the marker and assists in placing the marker device on the marker holder in a force fit and/or positive fit.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (for example on the surface of) a characteristic anatomical structure of the body part can also represent said structure. The landmark can represent the anatomical structure as a whole or only a point or part of it. A landmark can also for example lie on the anatomical structure, which is for example a prominent structure. An example of such an anatomical structure is the posterior aspect of the iliac crest. Another example of a landmark is one defined by the rim of the acetabulum, for instance by the center of said rim. In another example, a landmark represents the bottom or deepest point of an acetabulum, which is derived from a multitude of detection points. Thus, one landmark can for example represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational center of the femur when moved relative to the acetabulum.

Description of the Figures

In the following the invention is described with reference to the appended Figures which represent specific embodiments of the invention. The scope of the invention is however not limited to the specific features disclosed in the context of the Figures, wherein A first embodiment of the disclosed tracking system comprises a first camera 4 that is embodied as a microscope-integrated video-camera which forms part of the medical microscope 8 and is integrated within the housing of the microscope 8. The microscope 8 is coupled to an articulated arm of a mobile trolley which contains a computer 3 the processor of which is adapted to perform all of the method-steps described performed in the context of the present invention. It becomes apparent from FIG. 1 that the microscope 8 can be arranged with respect to a medical workspace adjacent to a patients head 2 in any desired manner, such that the microscope-integrated camera 4 can be utilized for tracking the instrument 1 within the medical workspace. As it can be seen in FIG. 1, the instrument 1 is not fitted with any specific tracking markers. Rather the spatial position of instrument 1 within the coordinate system of camera 4 is determined by analyzing the contours of the instrument 1 within a monoscopic video image obtained from camera 4.

For determining the relative position between the anatomical structure 2 and camera 4, a second video camera 5 is provided at a fixed position with respect to the microscope 8 and video camera 4. In a corresponding manner, a tracking marker 7 having a checkerboard pattern is provided at a fixed spatial position with respect to the anatomical structure 2. In a specific embodiment, the anatomical structure is a head, wherein the tracking marker 7 is fixedly attached to a Mayfield-Clamp that immobilizes the patient's head 2. As soon as the tracking marker 7 can be recognized by the second optical camera 5, the position of the tracking marker 7 within the coordinate system of tracking camera 5 can be calculated in the same manner as the position of instrument 1 within the coordinate system of camera 4 is determined, and, as soon as the position of camera 4 with respect to camera 5 is known, the position of both, instrument 1 and tracking marker 7 can be transformed into one common coordinate system. After an image dataset of the anatomical structure (head) 2 has been registered with the actual anatomical structure (head) 2, a medical navigation system is able to calculate and display a correct positional alignment of a virtual representation of the instrument 1 with respect to an image-representation of the anatomical structure (head) 2 FIG. 2 shows a second embodiment, differing from the first embodiment shown in FIG. 1 only by an inverted arrangement of the tracking marker 7 and the second video camera 5. While tracking marker 7 is fixedly coupled to the microscope 8 and camera 4, the second camera 5 is coupled to the anatomical structure 2. Additionally, camera 5 can be pivoted between two known orientations, one orientation allowing camera 5 to recognize tracking marker 7 and the other orientation allowing camera 5 to recognize the anatomical structure 2 and instrument 1 for registration purposes.

Figure 2:
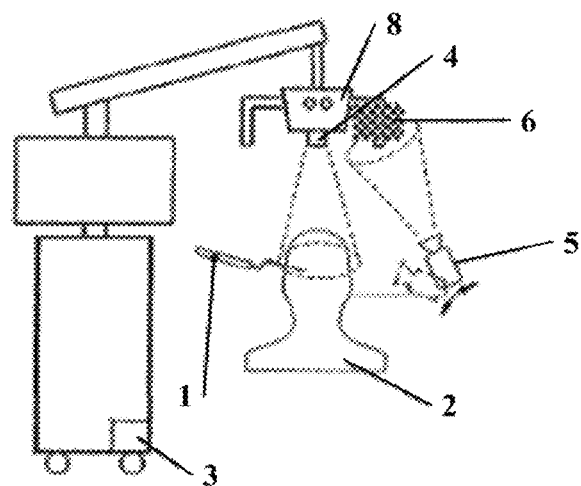
FIG. 2 shows a second embodiment of the disclosed tracking system.
Figure 3:
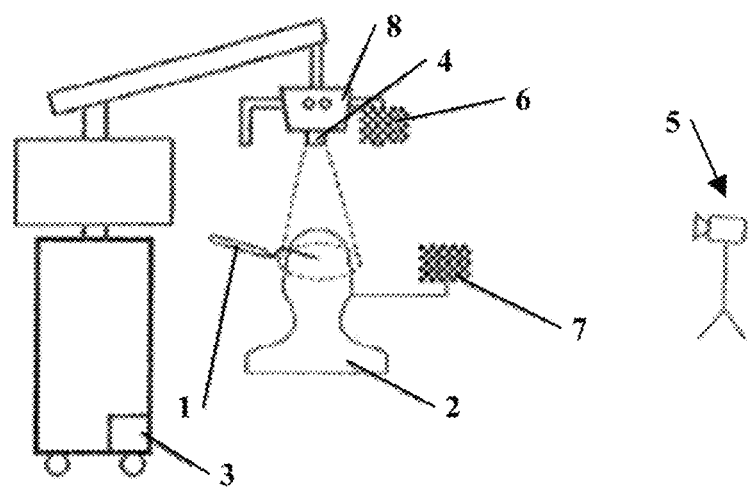
FIG. 3 shows a third embodiment of the disclosed tracking system.

FIG. 3 shows a third embodiment of the inventive system, which differs from the embodiment shown in FIGS. 1 and 2 only in that camera 5 is provided as an "external" video camera that is neither fixedly coupled to the anatomical structure 2 nor to the microscope's video camera 4. Instead, the anatomical structure 2 and the microscope 8 are both fitted with fixedly attached tracking markers 6 and 7, which both can be recognized by the external camera 5, so that in the end, the spatial position of the instrument 1 and tracking marker 7 can be transformed into a common coordinate system.

Figure 4:
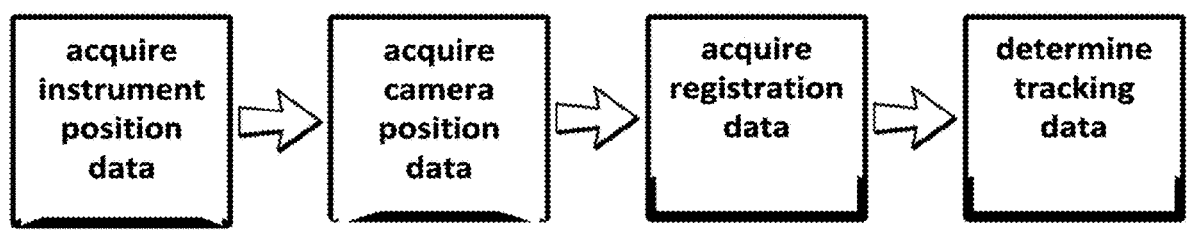
FIG. 4 shows a flow diagram comprising the basic steps of the disclosed method.

FIG. 4 shows the basic method-steps which are performed in the context of the inventive tracking method. In the following, a rather specific approach for tracking at least one medical instrument 1 with respect to an anatomical structure 2 is described without limiting the claimed subject-matter to any specific embodiment.

Prior to treatment of the patient, a three-dimensional scan of the patient's body/anatomical structure is performed, for obtaining a three-dimensional image dataset. After the patient's head is immobilized by a Mayfield-Clamp, the microscope 8 is positioned such that the microscope-integrated camera 4 can observe the medical workspace containing the anatomical structure 2 and the instrument 1. The microscope zoom may then be set to a minimum so that it can observe the patient's head during the following registration procedure. Further, the second video camera 5 is adjusted to observe the corresponding tracking marker(s) 6, 7.

For registration purposes, a landmark registration may be performed by palpating a plurality of landmarks with a tracked pointer tool 1. Each of the landmarks is palpated with the pointer 1 and, as pointer 1 can be seen in the microscope video image, computer 3 connected to both cameras 4 and 5 is able to calculate the spatial position of each of the landmarks with respect to the microscope. As the relative position of the microscope and a patient-invariant coordinate system can be calculated from the video image of camera 5, the spatial position of each of the landmarks can be transformed into a patient-invariant coordinate system.

The registration procedure ultimately provides the necessary transformation between the patient-invariant coordinate system and a coordinate system assigned to the image dataset.

After the registration has been completed, the patient is prepared for a treatment procedure. The microscope may be removed from the patient and may be draped with a sterile drape. In case the second video camera 5 is coupled to the anatomical structure 2, it may be removed for draping or be replaced by a sterile camera, which may have a sterile housing or which may be provided as disposable article. Further, the patient is draped, as well.

After the preparation procedure the microscope 8 is then positioned next to the anatomical structure 2 again and its spatial position with respect to the anatomical structure can be determined. Based on the data describing the relative position between the microscope and the patient-invariant coordinate system, and the data regarding the microscope's zoom and focus, the field of view of the microscope image can be calculated with respect to the patient-invariant coordinate system. Based on the registration data which describes the transformation between an image-invariant coordinate system and a patient-invariant coordinate system, the spatial position of the instrument 1 which is tracked by the microscope-integrated camera 4 can be determined with respect to the actual anatomical structure 2.

Part II: Instrument Ring Marker with Contour

General Description

In this section, a description of the general features of the present invention is given for example by referring to possible embodiments of the invention.

In general, the invention reaches the aforementioned object by providing a medical instrument with tracking markers running around the instrument's body portion at different diameters. Generally speaking, the inventive medical instrument has a body section and at least three tracking markers which are adapted to be recognized by an optical tracking system comprising at least one camera, and which run circumferentially around the body section, wherein at least one first tracking marker encompasses a first cross-sectional area around the body section and at least one second tracking marker encompasses a second cross-sectional area around the body section. The size of the first cross-sectional area differs from the size of the second cross-sectional area.

Each one of the tracking markers may also have a predetermined color, wherein it is also conceivable that different tracking markers have different colors. More specifically, the instrument may have at least one group of tracking markers comprising three tracking markers, wherein the central tracking marker of each group may be color coded, for example by having a different color than the remaining markers of said group.

One embodiment of the medical instrument has at least one tracking marker that is disposed on the outer surface of the body section, for example by being printed onto the surface of the instrument. On the other hand, each one of the tracking markers may be provided at a separate structure that runs around the central instrument body in a ring-like manner with a circumferential gap between the structure and the instrument body.

Each of the cross-sectional areas around which a tracking marker is provided may have an arbitrary form.

According to a more specific embodiment, at least one or all of the cross-sectional areas have a substantially circular form, so that the corresponding tracking markers have a circular shape, as well.

Moreover, the instrument's body section may have an elongated shape and the at least three tracking markers are disposed along a longitudinal axis of the body section. In other words, the tracking markers are provided on the instrument in a row, such that the distance between each of the tracking markers is measured along the longitudinal axis of the instrument via an optical tracking system. Further, the instrument's body section may have a rotationally symmetric shape, with the longitudinal axis being the symmetry axis of the body section and of the tracking markers.

A further embodiment of the medical instrument comprises a functional section adapted to act on an anatomical structure of a patient and/or a handle section adapted to be grasped by a person. In other words, the medical instrument may be provided with features of a medical treatment instrument or surgical instrument, such as a tool tip or blade being provided at a known distance with respect to the tracking markers. On the other hand, the instrument may be embodied as a mere tracking portion which is adapted to be attached to a corresponding medical treatment tool or surgical tool in any conceivable manner, such that the position of the instrument can be determined via the trackable having the ring-shaped tracking markers.

For that reason, the instrument may have a cavity that is adapted to receive a portion of the other medical instrument to be tracked. This cavity may extend along the symmetry axis of the instrument and is adapted to receive a rotationally symmetrical portion of the other medical instrument. Consequently, the central axis of the instrument the tracking portion is attached to is concentrically surrounded by the tracking markers.

Further, the inventive instrument may comprise an arbitrary number of tracking markers, groups of which may have the same diameter.

A further aspect of the present invention relates to a medical tracking method for tracking a medical instrument as described herein, the method comprising executing, on a processor or a computer, the steps of:

Acquiring, at the processor, distance data describing the distance between at least three tracking markers;

Determining, by the processor and based on the distance data, position data describing the spatial location and/or orientation of the medical instrument with respect to at least one camera of a medical tracking system recognizing the tracking markers.

Such method may involve any of the features described above in the context of the inventive instrument.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said embodiment.

Definitions

In this section definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical)

analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer.

Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a marker to be detected by a marker detection device in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

Description of the Figures

Figure 5:
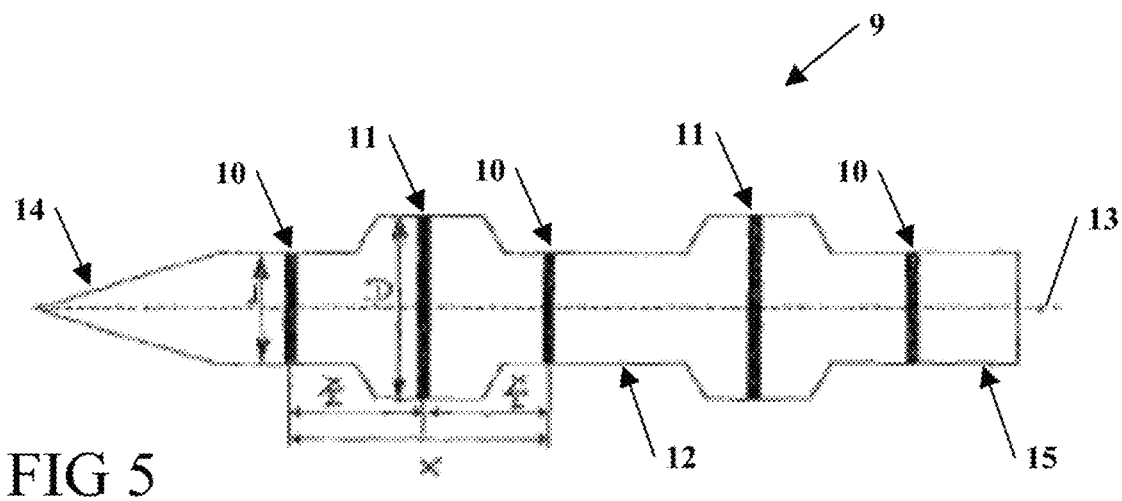
FIG. 5 shows a side-view on a first embodiment of the instrument.

In the following, the invention is described with reference to the appended Figures which represent a specific embodiment of the invention. The scope of the invention is however not limited to the specific features disclosed in the context of the Figures, wherein FIG. 5 shows a specific embodiment of the inventive instrument having a rotationally symmetric instrument body 9 with a tip-portion 14, a handle-portion 15 and an intermediate tracking-portion with three circumferential tracking markers 10 having a smaller diameter d and two circumferential tracking markers 11 having a larger diameter D. Each of the tracking markers 10 and 11 is provided directly on the outer surface of the instrument body 9 and may be for example printed or lasered onto the surface. It can be taken from FIG. 5 that the three most distal tracking markers 10 and 11 are spaced apart from each other at the same distance (denoted x/2), so that the central larger tracking marker 11 is provided right at the middle between the two smaller tracking markers 10. Consequently, the two smaller tracking markers re spaced from each other by a distance x.

Figure 6:
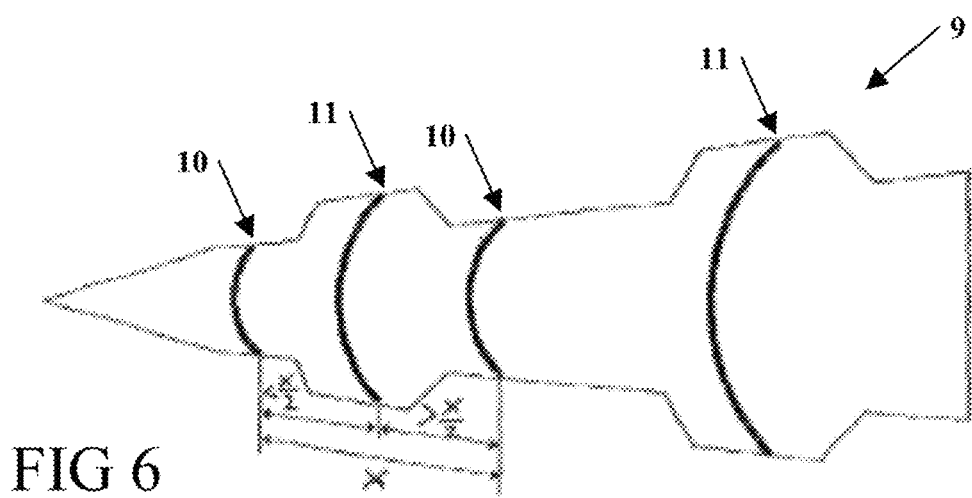
FIG. 6 schematically shows a perspective view on the embodiment shown in FIG. 5.

FIG. 6 schematically shows a perspective view on the instrument and it can be seen that from this perspective that the central, larger tracking marker 11 appears to be, within the image plane, positioned closer to the most distal, smaller tracking marker 10 and further apart from the more proximal tracking marker 10. This perspective effect will help an optical tracking system to recognize and calculate the spatial orientation more accurately by measuring the distance between the tracking markers in a direction which is parallel to the longitudinal axis 13 of the instrument. The tilting angle can even be determined using tele-centric lenses. For such lenses the object size is independent from the object distance. Experiments have shown that the ring markers can be sufficiently recognized by having a width in the image-plane of at least two pixels.

Further, the inventive tracking approach may involve an edge detection method according to Canny, Sobel, LaPlace, or similar of the outer contour of the instrument. This edge detection allows to determine the central axis of a cylindrical instrument in FIG. 5 to 9, about which the distance or intersection between the tracking markers can be determined for example by

- detecting the outer contours of the tracking markers by using, for example, edge detection algorithms according to Canny, Sobel, LaPlace or similar. Subsequently, the intersections/distances between the ring marker edges are determined together with the central axis of the instrument.
- It is the particular color channel of each ring corresponding histogram used at marker to the position of the marker ring on the central axis to determine.

Figure 7:
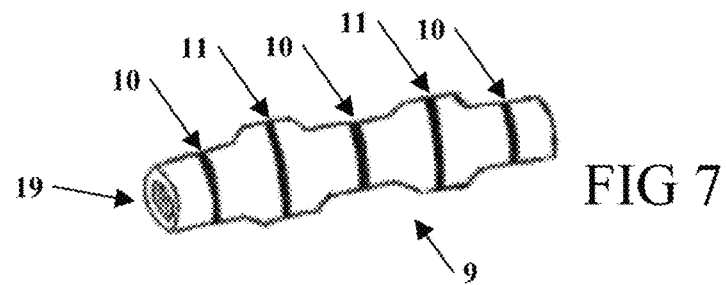
FIG. 7 shows a perspective view on a second embodiment of the inventive instrument.
Figure 8:
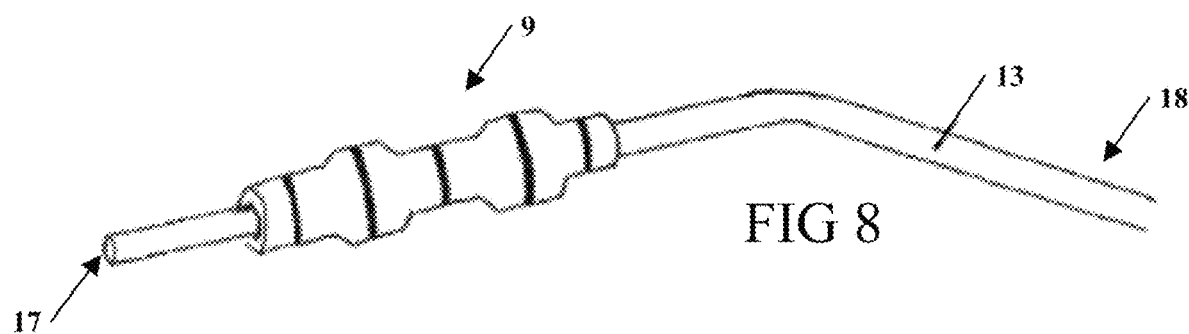
FIG. 8 shows the embodiment of FIG. 7 attached to another medical instrument.

FIG. 7 shows a second embodiment of the inventive instrument which acts as a marker portion that can be releasably attached to an instrument to be tracked. This second embodiment has substantially the same features as the instrument shown in FIGS. 5 and 6, except for the central cavity 19 which is adapted to receive a longitudinal, cylindrical portion of a suction-tool 16 having an orifice 17 and a handle section 18 as shown in FIG. 8.

Figure 9:
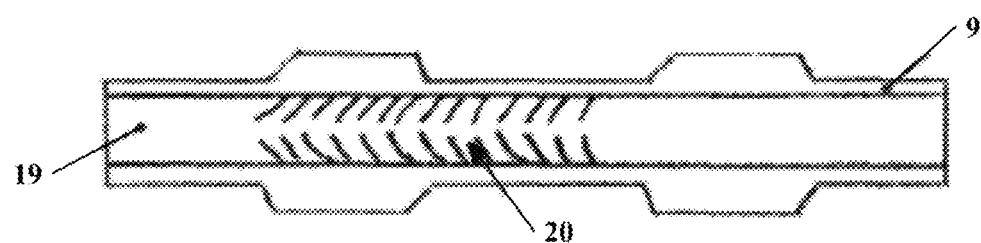
FIG. 9 shows a cross-sectional view through the embodiment shown in FIGS. 7 and 8.

FIG. 9 shows a cross-sectional view of this second embodiment. Within the central cylindrical cavity 19, an array of resilient members are provided, which will fixedly hold the instrument body 9 at a fixed position around tool 16. It is important to note that, additionally or alternatively, any conceivable means for attaching the instrument body 9 on a surgical tool may be also be provided, for example magnetic means, adhesive means or any means which provide a friction fit or form fit between the instrument body 9 and a tool received within cavity 19.

Specific Examples

A medical instrument having a body section 9 and at least three tracking markers 10, 11 which are adapted to be recognized by an optical tracking system comprising at least one camera, and which run circumferentially around the body section 9, wherein at least one first tracking marker 10 encompasses a first cross-sectional area around the body section 9 and at least one second tracking marker 11 encompasses a second cross-sectional area around the body section 9, and wherein the size of the first cross-sectional area differs from the size of the second cross-sectional area.

Wherein at least one of the tracking markers 10, 11 is disposed on the outer surface 12 of the body section 9.

Wherein at least one of the cross-sectional areas has a substantially circular shape.

Wherein the body section 9 has an elongated shape and the at least three tracking markers 10, 11 are disposed along a longitudinal axis 13 of the body section 9.

Wherein the body section 9 has a rotationally symmetric shape, with the longitudinal axis 13 being the symmetry axis of the body section 9 and of the tracking markers 10, 11.

Further comprising a functional section 14 adapted to act on an anatomical structure of a patient, and/or a handle section 15 adapted to be grasped by a person.

Wherein the instrument is adapted to be releasably attached to another medical instrument 16 comprising a functional section 17 adapted to act on an anatomical structure of a patient, and/or a handle section 18 adapted to be grasped by a person. The instrument having a cavity 19 adapted to receive a portion of the other medical instrument 16.

Wherein the cavity 19 extends along the symmetry axis 13 of the instrument and is adapted to receive a rotationally symmetrical portion of the other medical instrument 16.

The instrument comprising a plurality of first tracking markers 10 encompassing smaller cross-sectional areas, particularly cross-sectional areas of substantially the same size and/or a plurality of second tracking markers encompassing larger cross-sectional areas, particularly cross-sectional areas of substantially the same size.

Part III: Attachable Marker Sticker

General Description

In this section, a description of the general features of the present invention is given for example by referring to possible embodiments of the invention.

In general, the invention reaches the aforementioned object by providing a medical tracking marker that is adapted to be recognized by an optical tracking system that comprises at least one camera, wherein the tracking marker predominantly extends in one spatial direction and comprises at least one recognition section that is adapted to produce at least one orientation dependent optical pattern along said spatial direction. In other words, the medical tracking marker may have one or more recognition sections that predominantly extend in the same direction, wherein each of the recognition sections provides at least one orientation dependent pattern in this direction.

The surface of the recognition section may have any desired shape. For example, the recognition section's surface may be substantially flat, but, the surface may also have a curved shape. The surface may even adapt to the surface of an object such as a medical instrument to which the marker is attached.

Further, the tracking marker, particularly the at least one recognition section of the tracking marker exclusively provide one or more orientation dependent optical patterns in the spatial direction the optical tracking marker predominantly extends in. Such a tracking marker is especially suitable for being attached to an elongated instrument or an elongated instrument section, since the tracking marker will very well adapt to the elongated shape and does not form a disturbing and bulky object on the instrument. A further example for the inventive tracking marker comprises an attachment section or attachment surface that is adapted to contact an object to be tracked. For example, the attachment section may be provided on a face of the marker that faces away from the face of the recognition section. Further, this surface or section may have adhesive or magnetic properties or may even form an open cross-section that encompasses a cavity for receiving an object in a form-fit-manner. However, the medical tracking marker may also be attached to an object/instrument via any suitable means, for example screws or rivets. Further, the marker may even be integrally formed with the instrument to be tracked. Moreover, the attachment surface may have a shape that defines an orientation of the at least one orientation dependent optical pattern with respect to the medical instrument. For example the attachment surface may form a longitudinal groove with a central axis, wherein the central axis is parallel to the spatial direction in which the marker predominantly extends in and along which the at least one recognition section provides the optical pattern. Imagining a longitudinal, for example, cylindrical instrument to be provided with the inventive tracking marker is received in this longitudinal groove, the at least one optical pattern will automatically be aligned parallel to the instrument's longitudinal axis. This will allow to precisely determine the instrument's orientation in a plane which is defined by the line of sight between an optical camera and the recognition section, and the instrument's longitudinal axis.

Further, the tracking marker may have a rigid structure or "body". This structure may however also be mechanically flexible in the case of a "clip-on"-marker, or may even be a foil that takes the form of an object to which it may be adhesively attached.

Since, as already described above, each orientation dependent optical pattern allows to derive therefrom only a certain amount of orientation information, a further example of the inventive tracking marker may comprise additional tracking fiducials adapted to be optically recognized by a camera of an optical tracking system. For example the marker may comprise at least two tracking fiducials which mark at least one predefined spatial distance which can be measured with the help of an optical tracking system.

In a second aspect, the invention is directed to a computer implemented medical method or program for tracking at least one object within a medical workspace, which has been provided with at least one medical tracking marker as described above. Basically, the method comprises executing, on at least one processor of at least one computer, the following exemplary steps which are executed by the at least one processor. In a (for example first) exemplary step first tracking data is acquired that describes the spatial orientation of the object, wherein the recognition section is recognized by an optical tracking system that comprises at least one camera. In other words, a first part of the overall amount of tracking information used for tracking an object is derived from evaluating information obtained from an image showing the recognition section, which is provided by at least one camera of an optical tracking system.

In a further (for example second) exemplary step, second tracking data is acquired which describes the spatial location and/or orientation of the object by recognizing at least one optically determinable fiducial (which differs from the at least one recognition section and) which is assigned to the tracking marker and/or to the object the tracking marker is attached to. In other words, a second part of the overall tracking information used for tracking the instrument is obtained from evaluating the camera image with respect to additional optically recognizable features or fiducials of the tracking marker itself or of an object the tracking marker is attached to. As already referred to above, this recognition may involve known computer vision algorithms like edge detection, Hough transformation, line segment detection etc. The additional features/fiducials may be inherent features of the marker or the object and may be derivable from the visual appearance of the marker/object. This would be the case with any optically determinable edge of the marker body or object body. Further, the additional features may be "artificial", which means that the marker and/or object are provided with specific and optically determinable tracking features such as optical patterns or color coding, which may be printed directly onto the marker/object-surface or may be provided in the form of stickers.

In a further (for example third) exemplary step, the first tracking data and the second tracking data is used for determining/calculating position data that describes the spatial position of the object to be tracked. In other words, the first amount and the second amount of information is combined to obtain the information needed to track the instrument. Even though a "full" six-dimensional acquisition of an object position may be desirable under certain circumstances, the content of the combined information may as well be limited to the amount of information needed for a certain purpose. For example, the rotational degree of freedom around the central axis of an elongated and entirely cylindrical object such as a needle may not be of interest, so that the tracking information may only describes the instrument position in five degrees of freedom. Nevertheless, the present invention may consider any desired number of dimensions/degrees of freedom of the object to be tracked.

In a further example, the first tracking data exclusively contains information describing an angular orientation of the tracking marker within a plane defined by said spatial direction (longitudinal axis) and the line of sight between the recognition section and the camera of the tracking system. In other words, the at least one recognition section of the tracking marker is only utilized for determining the tilting angle of the tracking marker with respect to a tracking camera that provides an image of the orientation dependent optical pattern. The tilting angle is thereby determined within the plane that includes the longitudinal axis of the tracking marker/the object fitted with the tracking marker, and a line connecting the camera and the recognition section. The remaining information as to the spatial location and/or orientation of the tracking marker/object is then determined in a different manner, by evaluating the appearance of further tracking features/fiducials seen the in the camera image.

In a more specific example of the invention, the first tracking data is acquired only within predetermined limits of the angular orientation with respect to the line of sight. For example, these limits may be set with respect to a "zero position" defined by the longitudinal axis of the tracking marker/object being perpendicular to the line of sight between the camera and the recognition section. In case the angular orientation of the marker is not within these predetermined limits, the determination of markers/objects orientation may be determined based on recognizing other features/fiducials/tracking markers seen in the camera image, rather than by recognizing the recognition section.

In one further example, the information as to the spatial location and/or orientation of the object, which is not acquired from recognizing the recognition section, is acquired from recognizing the at least one optically determinable fiducial of the tracking marker and/or the object. In other words, this information may be obtained from the second tracking data.

In an even further and more specific example of the method, it is conceivable that the:

tracking data describing the spatial location and orientation of the tracking marker and/or the object within a plane that is perpendicular to the line of sight between the tracking marker and/or the object and a camera of the tracking system is acquired, involving recognizing the at least one optically determinable fiducial of the tracking marker and/or the object;

tracking data describing the spatial orientation of the tracking marker and/or the object within a plane defined by the spatial direction and the line of sight between the recognition section and the camera is acquired, involving recognizing the recognition section; and tracking data describing the spatial location of the tracking marker and/or the object along the line of sight between the recognition section and the camera of the tracking system is acquired, involving recognizing at least two tracking fiducials adapted to mark at least one predefined distance, which are optically recognized by the optical tracking system.

This approach allows to determine the spatial position of the tracking marker/object in at least five dimensions.

In a third aspect, the invention is directed to a non-transitory computer-readable storage medium on which the program according to the second aspect is stored.

In a fourth aspect, the invention is directed to at least one computer (for example, a computer), computer at least one processor (for example, a processor) and at least one memory (for example, a memory), wherein the program according to the second aspect is running on the processor or is loaded into the memory, or wherein the at least one computer comprises the program storage medium according to the third aspect.

Definitions

In this section definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™ A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

The invention also relates to a navigation system for computer-assisted surgery, comprising: the computer of the preceding claim, for processing the absolute point data and the relative point data;
a detection device for detecting the position of the main and auxiliary points in order to generate the absolute point data and to supply the absolute point data to the computer, a data interface for receiving the relative point data and for supplying the relative point data to the computer, and
a user interface for receiving data from the computer in order to provide information to the user, wherein the received data are generated by the computer on the basis of the results of the processing performed by the computer.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows to determine the relative position in up to three rotational dimensions and up to three translational dimensions from a single two-dimensional image.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

Description of the Figures

In the following the invention is described with reference to the appended Figures which represent a specific embodiment of the invention. The scope of the invention is however not limited to the specific features disclosed in the context of the Figures, wherein FIG. 10 shows a first embodiment of a medical tracking marker 27 according to the present invention, which has an elongated shape that predominantly extends in a spatial direction L. The structure or body of the tracking marker 27 has on its flat face facing upwards a recognition section 21 within which an orientation dependent optical pattern 22 is provided. This orientation dependent optical pattern depends on the viewing direction on the recognition section 21. The optical pattern 22 will change its appearance as soon as the viewing direction is changed.

Consequently, the tilting angle of the tracking marker 27 with respect to the viewing direction can be derived from the appearance of the optical pattern 22. Additionally to the recognition section 21 including the optical pattern 22, the upper side of the tracking marker 27 further has two tracking fiducials 25 which are also optically recognizable, and which define a predetermined distance between them. As the distance between the fiducials 25 is known, the distance between the tracking marker 27 and an optical camera of a medical tracking system can be derived from the distance between the fiducials 25 as seen in an image provided by that camera.

At the bottom side of the tracking marker 27, which is opposite to the upper side containing the recognition section 21, an attachment surface 23 of the tracking marker 27 is provided, which forms a cylindrical groove that in turn defines a central axis A. As can be seen in FIG. 21, the central axis A runs parallel to the longitudinal direction of the tracking marker 27 and if the recognition section 1.

As soon as the tracking marker 27 is attached to an elongated instrument 24 received within the groove and contacted by the attachment surface 23, the longitudinal direction L of the recognition section 21 will be automatically aligned with the longitudinal axis of the instrument 24.

This is demonstrated in FIG. 11, showing a cylindrical instrument 24 fitted with the tracking marker 27, wherein the longitudinal axes of the instrument 24 and the recognition section 21 run parallel. By way of example, FIG. 11 shows optically determinable fiducials 26 which are defined by edges of the instrument 24 as seen in a two-dimensional camera image, which may be used in addition to the recognition section 21 and the fiducials 25 to determine the spatial position of the instrument 24, specifically by way of computer vision algorithms. Additionally or alternatively to the "instrument edges" 26, any optically recognizable fiducials may be determined, such as any of the edges of the tracking marker 27.

FIG. 12 shows an alternative embodiment of the inventive tracking marker 27, which is formed as an attachable marker sticker having a foil-like structure that adapts to the instrument's cylindrical surface after it has been put on the instrument 24. Just like the first embodiment shown in FIGS. 10 and 11, the second embodiment comprises a recognition section 21 that provides an orientation dependent optical pattern 22, and two optically recognizable fiducials 25 on its upper face.

Figure 13:
FIG. 13 shows a flow diagram containing the basic steps of the disclosed method.

FIG. 13 shows a flow diagram illustrating the basic steps of the disclosed method which, in the illustrative example of FIG. 10, starts with a step of acquiring first tracking data. Then, a step is executed which encompasses acquiring the second tracking data. In a subsequent step, the first tracking data and the second tracking data are used as a basis for calculating the position data which describes the spatial position of the object 24.

Specific Examples

A medical tracking marker being adapted to be recognized by an optical tracking system comprising at least one camera, and predominantly extending in one spatial direction L, comprising at least one recognition section 21 that is adapted to produce at least one orientation dependent optical pattern 22 along said spatial direction L.

Wherein the recognition section 21 is substantially flat.

The medical tracking marker exclusively providing orientation dependent optical pattern(s) 22 along said spatial direction L.

Further comprising an attachment surface 23 for contacting the surface of a medical instrument 24 the tracking marker is attached to, particularly wherein the attachment surface 23 has adhesive or magnetic properties, or forms an open cross-section that encompasses a cavity.

Wherein the attachment surface 23 has a shape that defines an orientation of the at least one orientation dependent optical pattern 22 with respect to the medical instrument 24.

Wherein the attachment surface 23 forms a groove having a central axis A, the central axis A being parallel to the spatial direction L.

Wherein the tracking marker 27 has a mechanically flexible structure, particularly a foil-like structure.

Further comprising at least two tracking fiducials 25 adapted to mark at least one predefined spatial distance which can be optically recognized by the optical tracking system.

A computer implemented medical method for tracking an object 24 within a medical workspace, the object 24 being provided with at least one medical tracking marker 27 which comprises at least one recognition section 21 that is adapted to produce at least one orientation dependent optical pattern 22 along a spatial direction L, the method comprising executing, on a processor of a computer, the steps of:
- acquiring, at the processor, first tracking data describing the spatial orientation of the object 24, involving recognizing the recognition section 21 using an optical tracking system comprising at least one camera;
- acquiring, at the processor, second tracking data describing the spatial location and/or orientation of the object 24, involving recognizing at least one optically determinable fiducial 25, 26 of the tracking marker 27 and/or the object 24, the at least one optically determinable fiducial 25, 26 being different from the recognition section 21;
- determining, by the processor and based on the first tracking data and the second tracking data, position data describing the spatial position of the object 24.

Wherein the first tracking data exclusively contains information about an angular orientation of the tracking marker 27 within a plane defined by the spatial direction and the line of sight between the recognition section 21 and a camera of the tracking system.

Wherein the first tracking data is acquired only within predetermined limits of the angular orientation with respect to the line of sight.

Wherein information as to the spatial location and/or orientation of the object 24, which is not acquired from recognizing the recognition section 21, is acquired from recognizing the at least one optically determinable fiducial 25, 26 of the tracking marker 27 and/or the object 24.

Wherein
- tracking data describing the spatial location and orientation of the tracking marker 27 and/or the object 24 within a plane that is perpendicular to the line of sight between the tracking marker 27 and/or the object 24 and a camera of the tracking system is acquired involving recognizing the at least one optically determinable fiducial 25, 26 of the tracking marker 27 and/or the object 24; tracking data describing the spatial orientation of the tracking marker 27 and/or the object 24 within a plane defined by the spatial direction L and the line of sight between the recognition section 21 and the camera is acquired involving recognizing the recognition section 21; and
- tracking data describing the spatial location of the tracking marker 27 and/or the object 24 along the line of sight between the recognition section 21 and the camera of the tracking system is acquired involving recognizing at least two tracking fiducials 25 adapted to mark at least one predefined distance, which are optically recognized by the optical tracking system.

A non-transitory computer-readable storage medium storing a computer program which, when executed on a processor of a computer or loaded into the memory of a computer, causes the computer to perform a method.

A computer comprising the non-transitory computer-readable program storage medium.

Part IV: Gray Scale Marker Tracking

General Description

In this section, a description of the general features of the present invention is given for example by referring to possible embodiments of the invention.

In general, the invention reaches the aforementioned object by providing a medical tracking marker having at least one recognition section that produces at least one orientation dependent optical pattern, the recognition section having a face with lower areas and higher areas arranged in alternation, the lower areas being optically dark and the higher areas being optically bright, or vice versa. In other words, the at least one recognition section of the medical tracking marker comprises a face, particularly a single face, that has, viewed in a transverse cross-section through the recognition section, two groups of optically visible areas, wherein one of the two groups is provided above the other one of the two groups, such that the two groups are spaced from each other, and the upper one is therefore, by a certain distance, "closer" to a camera of a medical tracking system which is targeted on the tracking marker. Since the lower areas are thereby located at the bottom of recesses formed between the higher areas, the visibility of the lower areas highly depends on the viewing direction onto the recognition section, whereas the visibility of the higher areas remains substantially unchanged. This results in a variable overall appearance of the recognition section, depending on the viewing direction onto the recognition section. For example, with the lower areas being white (optically bright) and the higher areas being black (optically dark), the appearance of the recognition section will be maximally bright when being looked upon from a direction that is perpendicular to the extension of the recognition section. With an increasing deviation from this perpendicular viewing direction, the recognition section will appear increasingly darker. With the lower areas being optically dark, for example black, and the higher areas being optically bright, for example white, this effect is of course inverted. The higher and lower areas need not be black and white, but may have any desired brightness or darkness or may even have different colors, as long as an orientation dependent difference in the overall appearance of the recognition section, when viewed from different directions, can be sufficiently recognized. In case the geometric arrangement of the higher and the lower areas is the same for all of the higher and lower areas of the recognition section, the optical appearance of the recognition section will be substantially homogenous over the entire recognition section. In a further example of the tracking marker, the higher areas and/or the lower areas are substantially flat when viewed in a transverse cross-section through the recognition section. In an even further example, the higher areas and/or the lower areas are arranged in parallel when viewed in a transverse cross-section through the recognition section. Each of the higher and the lower areas may therefore extend exclusively in two layers which lie above each other and may consequently form an alternately stepped cross-section of the recognition section.

In a further example, the lower areas and the higher areas have a longitudinal shape and are arranged in parallel. With such corrugated or ridged arrangement of the higher and the lower areas, a change of the viewing direction in a plane that is parallel to the corrugations or ridges will have almost no impact on the appearance of the recognition section, whereas a change of the viewing direction in a further plane which is perpendicular to the aforementioned plane will have the highest influence on the optical appearance. Alternatively, the higher and lower areas may be arranged in a curved manner, for example, in concentric circles.

In a further example, the face that comprises the lower areas and the higher areas is formed by the surface of a solid substrate or "body" of the tracking marker. This body or substrate may further be made from an opaque material. Alternatively, the face may be formed by a surface of an intransparent layer, particularly an intransparent foil, which has been applied onto the tracking marker.

An even further example of the inventive tracking marker further comprises a first, optically bright, and/or a second, optically dark reference section which provide, for each lighting situation, a reference appearance for an optical tracking system. The at least one reference section may be provided adjacent to the recognition section. Specifically, the recognition section may be flanked on either side by a first, for example optically dark reference section, and a second, for example optically bright reference section.

Further, the lower areas, particularly both, the lower areas and the higher areas, and specifically, the entire recognition section together with at least one reference section can be covered by a transparent layer that may have protective properties and the upper surface of which may be substantially flat.

In a second aspect, the invention is directed to a computer implemented medical method for tracking an object within a medical workspace, the object being provided with at least one medical tracking marker as described herein, which comprises at least one recognition section that produces at least one orientation dependent optical pattern. The method comprises the following steps, which are executed on at least one processor of at least one computer:

Acquiring brightness data describing the brightness of the recognition section recognized by at least one camera of an optical tracking system;

Determining, based on the brightness data, tracking data describing the angular orientation of the marker and/or the object with respect to the camera.

In other words, the orientation dependent optical appearance of at least one recognition section as seen in an image obtained from a camera of an optical tracking system is evaluated so as to derive therefrom the angular orientation of the marker and/or an object to which the marker is attached, with respect to the optical camera.

The step of determining tracking data may involve determining a reference brightness of at least one recognition section in order to take into account the current lighting situation that must not have an influence on the data describing the angular orientation of the marker with respect to the camera. Further, the step of determining tracking data may also involve comparing the recognized brightness of the recognition section with a predefined gray-scale chart. Such chart may provide, preferably unitary correlation between angular orientations and optical appearances of the recognition section.

In a third aspect, the invention is directed to a non-transitory computer-readable storage medium storing a computer program on a processor of computer are loaded into the memory of a computer, causes the computer to perform a method according to the second aspect.

In a forth aspect, the invention is directed to at least one computer (for example, a computer) comprising at least one processor (for example, a processor) and at least one memory (for example, a memory), wherein the program according to the second aspect is running on the processor or is loaded into the memory or wherein the at least one computer comprises the program storage medium according to the third aspect.

It is within the scope of the present invention to combine one or more features or one or more embodiments or aspects of the invention in order to form a new embodiment wherever this is technically expedient and/or feasible. Specifically, a feature of one embodiment which has the same or a similar function to another feature of another embodiment can be exchanged with said other feature and a feature of one embodiment which adds an additional function to another embodiment can for example be added to said other embodiment.

Definitions

In this section definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

The invention also relates to a navigation system for computer-assisted surgery, comprising the computer of the preceding claim, for processing the absolute point data and the relative point data;
a detection device for detecting the position of the main and auxiliary points in order to generate the absolute point data and to supply the absolute point data to the computer;
a data interface for receiving the relative point data and for supplying the relative point data to the computer, and
a user interface for receiving data from the computer in order to provide information to the user, wherein the received data are generated by the computer on the basis of the results of the processing performed by the computer.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows to determine the relative position in up to three rotational dimensions and up to three translational dimensions from a single two-dimensional image.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

Description of the Figures

Figure 14:
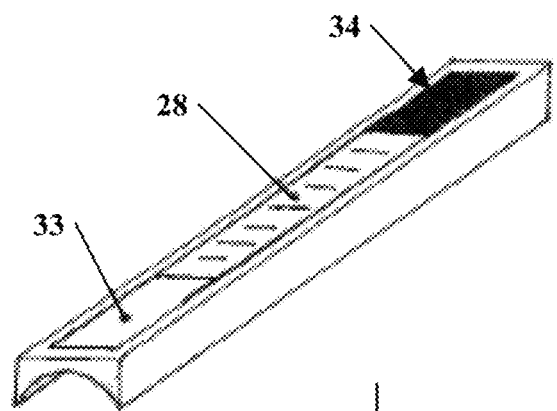
FIG. 14 shows a specific embodiment of the inventive tracking marker.

In the following; the invention is described with reference to the appended Figures which represent a specific embodiment of the invention. The scope of the invention is however not limited to the specific features disclosed in the context of the Figures, wherein FIG. 14 shows a specific embodiment of the inventive tracking marker 38 that has a solid substrate or body with a groove-shaped recess that can receive a correspondingly formed section of an elongated instrument 37 (shown in FIG. 16). On the top face of the tracking marker, which faces away from the recess, the tracking marker 38 comprises a recognition section 28 which provides an orientation dependent optical pattern. On both ends of the recognition section 28, reference sections 33 and 34 are provided, wherein a first reference section 33 is optically bright and a second reference section 34 is optically dark.

Figure 15:
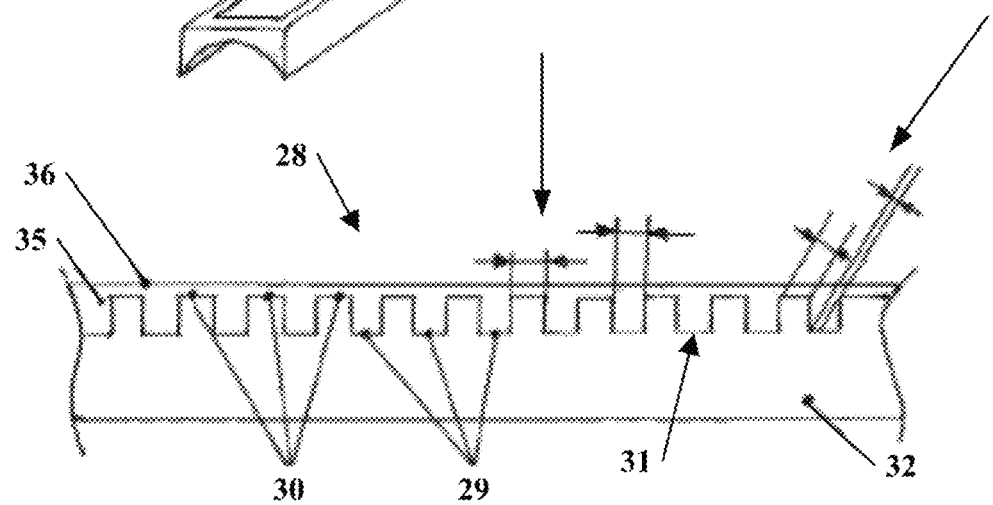
FIG. 15 shows a cross-sectional view through the recognition section of the marker as shown in FIG. 14.

It will become apparent from FIG. 15 that, as soon as the viewing direction on the recognition section 28 is changed within a plane containing the longitudinal axis of the tracking marker 38, the optical appearance of the reference section will also change, which allows determining the angular orientation of the tracking marker 38 and the instrument 37 with respect to an optical camera of an optical tracking system.

The recognition section 28 comprises an alternatingly stepped face that comprises higher areas 30 and lower areas 29. The higher areas 30 and the lower areas 29 define two separate layers which extend parallel to the longitudinal axis of the tracking marker 38 and of the instrument 37. Both groups of the higher areas 30 and the lower areas 29 are covered by a protected and transparent layer 35 which has a flat surface 36.

Figure 16:
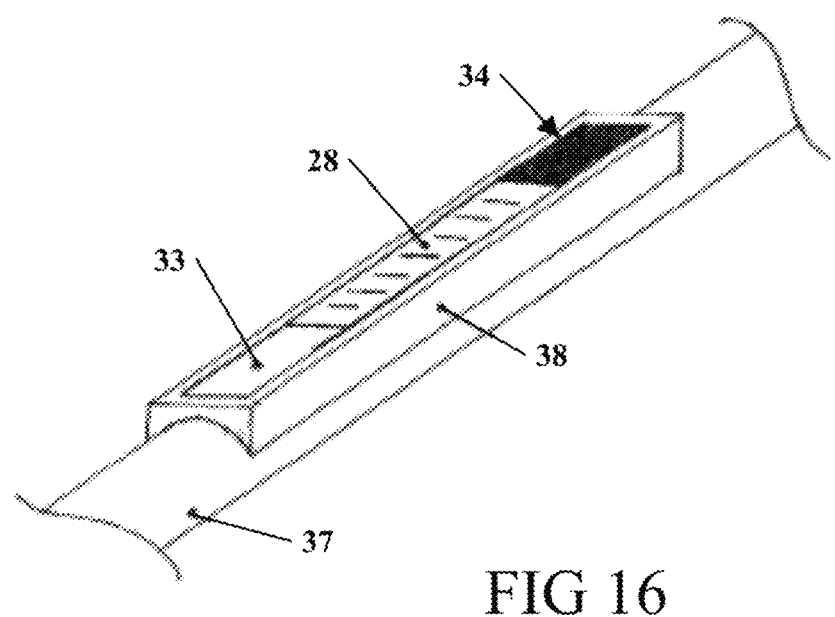
FIG. 16 shows the marker of FIG. 14 attached to an elongated medical instrument to be tracked.

Assuming that the lower areas 29 are optically dark, for example black, and the higher areas 30 are optically bright, for example white, the overall appearance of the recognition section 28 as seen in an image obtained from a camera which is aiming perpendicularly at the recognition section 28 from a distance (this viewing direction is represented by the left arrow shown in FIG. 15) will define a certain gray scale value, with the brighter areas 30 covering substantially the same amount of the overall area of the recognition section 28 than the darker areas 29. As soon as the viewing direction is changed and forms a more acute angle with the recognition section 28 (as represented by the right arrow shown in FIG. 15), the lower, darker areas 29 are obscured by the protruding sections on top of which the brighter areas are located, thereby decreasing the contribution of the dark areas 29 to a two-dimensional image made in this oblique direction, which finally will cause the recognition section 28 to appear brighter. In this context, this effect will be increased if the vertical sides of the protrusions, which extend perpendicularly to the lower and the higher areas 29 and 30 have the same or a similar brightness than the higher areas 30 on top of each of the protrusions. FIG. 16 shows the tracking marker from FIGS. 28 and 29 attached to an elongated cylindrical body of an instrument 37. Since the groove-shaped recess at the underside of the tracking marker extends in a direction perpendicular to the corrugations of the recognition section 28, the longitudinal axis of the instrument 37 will also extend in a direction perpendicular to these corrugations. This configuration maximizes the effect of a change in the instrument's angular orientation within the plane defined by the viewing direction and the longitudinal axis of the instrument on the optical appearance of the recognition section 28.

In order to "fully" determine the spatial position of the instrument 37, further tracking 10 information has to be acquired in addition to the information obtained from recognizing the recognition section 28 in any desirable manner, for example by methods and means described in Part III.

Figure 17:
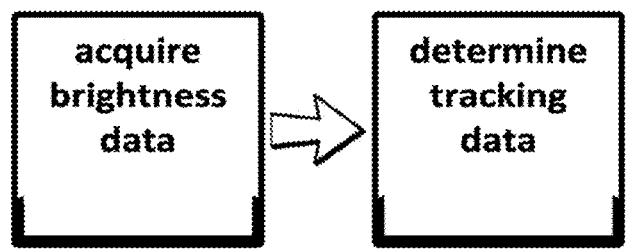
FIG. 17 shows a flow diagram comprising the basic steps of the disclosed method.

FIG. 17 shows the basic steps of the inventive method. In a first step, brightness data describing the brightness of the recognition section 28 is acquired as explained further above. From this data, the angular orientation of the instrument 37 within a plane defined by the longitudinal axis of instrument 37 and the viewing direction of a camera aiming at the tracking marker 38 can be derived.

Specific Examples

A medical tracking marker being adapted to be recognized by an optical tracking system comprising at least one camera, the tracking marker 38 comprising at least one recognition section 28 that produces at least one orientation dependent optical pattern, the recognition section 28 having a face 31 with lower areas 29 and higher areas 30 arranged in alternation, the lower areas 29 being optically dark and the higher areas 30 being optically bright, or vice versa.

Wherein, viewed in a transverse cross-section through the recognition section 28, the higher areas 30 and/or the lower areas 29 are substantially flat.

Wherein, viewed in a transverse cross-section through the recognition section 28, the higher areas 30 and/or the lower areas 29 are arranged in parallel.

Wherein the lower areas 29 and the higher areas 30 have a longitudinal shape and are arranged in parallel.

Wherein the face 31 is formed by the surface of a solid substrate 32.

Wherein the face 31 is formed by the surface of an intransparent foil.

Further comprising at least one of a first reference section 33 and a second reference section 34, one of the first reference section 33 and the second reference section 34 being entirely optically bright, and the other reference section 33, 34 being optically dark.

Wherein the recognition section 28 is flanked on either side by the first reference section 33 and the second reference section 34.

Wherein the lower areas 29, particularly the lower areas 29 and the higher areas 30, specifically the reference sections 33, 34 and the recognition section 28, are covered by a transparent layer 35.

Wherein the upper surface 36 of the transparent layer 35 is substantially flat.

A computer implemented medical method for tracking an object within a medical workspace, the object 37 being provided with at least one medical tracking marker 38 which comprises at least one recognition section 28 that produces at least one orientation dependent optical pattern, the 15 recognition section 28 having a face 31 with lower areas 29 and higher areas 30 arranged in alternation, the lower areas 29 being optically dark and the higher areas 30 being optically bright, or vice versa, the method comprising executing, on a processor of a computer, the step of:
acquiring brightness data describing the brightness of the recognition section 28 recognized by at least one camera of an optical tracking system;
 determining, based the brightness data, tracking data describing the angular orientation of the marker 38 and/or the object 37 with respect to the camera.

Wherein the step of determining tracking data involves comparing the recognized brightness of the recognition section 28 with a predefined grey-scale chart.

Wherein the step of determining tracking data involves determining a reference brightness of at least one reference section 33, 34, and comparing the recognized brightness of the recognition section 28 with the reference brightness.

A non-transitory computer-readable storage medium storing a computer program which, when executed on a processor of a computer or loaded into the memory of a computer, causes the 30 computer to perform a method.

A computer comprising the non-transitory computer-readable program storage medium.

Part V: Ring Marker Codification
General Description

In this section, a description of the general features of the present invention is given, for example by referring to possible embodiments of the invention.

In general, the invention reaches the aforementioned object by providing, in a first aspect, a computer-implemented method for identifying a medical device within a medical workspace, wherein the device has a body section and is provided with at least two markers adapted to be recognized by an optical camera, which run circumferentially around the body section. The method comprises executing, on at least one processor of at least one computer, the following exemplary steps which are executed by the at least one processor.

In a (for example first) exemplary step, codification data is acquired which describes at least one of the following.
 the number of the markers,
 the color of at least one marker,
 the width of at least one marker,
 the spacing between at least two markers.

In other words, the medical device is provided with at least two markers which are disposed on the body section of the device in a manner that is specific to the instrument. Since each of the markers is ring-shaped, an instrument-specific pattern provided by the marker arrangement can be obtained by a different number of the markers, predefined colors of the markers, different widths of the markers and different spacing between the markers. For example, a marker arrangement containing the at least two markers is a pattern which biuniquely describes one single specific device or instrument. On the other hand, it is conceivable that certain features of the marker arrangement give information about specific features of the corresponding instrument. For example, the number of the markers may give an indication about the diameter of an instrument shaft, whereas the spacing between the two most distal markers may give an indication about the length of the instrument. As a further example, the color of the most proximal marker may give an indication about the type of the instrument, whereas the width of the most proximal marker may give an indication about the type of the instrument. The present invention may therefore not only provide a biunique identification of a specific instrument, but may also or alternatively provide a nomenclature for specific features of the instrument.

In a (for example second) exemplary step, this codification data is then used to determine data that describes the actual properties of the device/instrument, which can then be used for image guided surgery. The data describing the instrument properties may be taken from a database or may be determined "directly" from the codification data. For example, the spacing between the for example two most distal markers of the marker arrangement may be exactly ⅒ of the overall length of the instrument portion extending from the marker arrangement.

In a further example, the codification data is acquired from an image showing the at least two markers, which has been obtained from an optical camera, for example a camera of a medical microscope or a medical tracking system.

Further, as already mentioned above, the step of determining device data describing the actual instrument or device may include the step of acquiring the device data from a database which may be stored on a computer assigned to the medical tracking system, wherein the database may further link the codification data and the device data.

In a further example, the device data that may be stored on a database comprises information as to at least the instrument/device type, the instrument manufacturer, the material properties of the instrument/device and/or the geometric properties of the instrument/device. Further, the database may further comprise information about the geometric properties of the instrument/device with respect to the markers, such that the markers may even further be utilized as tracking markers.

According to a further example of the present invention, the method further comprises the steps of acquiring data as to the spatial position of at least one of the markers, so that consequently, the at least one marker is utilized as a tracking marker. Based on the acquired marker position data and the data describing the geometric properties of the device, the spatial position of at least one part of the instrument/device can be calculated and forwarded to the medical navigation system. Again, the marker position data may be acquired from at least one image showing the marker array, obtained from the at least one optical camera.

It is also conceivable that the instrument/device is provided with more than one, for example two of the above described marker arrays, wherein a first marker array is adapted to be recognized by a medical tracking system comprising at least one, preferably two IR cameras, and a further marker array is adapted to be recognized by a conventional video camera of a microscope detecting visible (to the human eye) light. Additionally or alternatively, the codification data and the marker position data may be acquired from different cameras. While the codification data may be acquired from at least one camera of a medical microscope, the marker position data may be acquired from at least one camera of a medical tracking system.

In a second aspect, the invention is directed to a corresponding medical instrument or device having an elongated body section, which comprises at least one group or array of at least two markers adapted to be recognized by at least one optical camera, which run circumferentially around the body section, wherein the at least two tracking markers of at least one of the groups form a pattern providing a predetermined code for the properties of the device. In particular, the pattern may be formed by spatially concentrating the at least two markers to a specific position on the instrument.

As already described further above, the code may be based on at least one of the following features:
- the number of the markers,
- the color of at least one marker,
- the width of at least one marker,
- the spacing between at least two markers.

On the one hand, the code based on the above features may be a biunique code assigned to a single specific instrument or device. On the other hand, the code may give an indication as to specific properties of the instrument or device, such as manufacturer, type, length, material etc.

As the present invention provides a "slim" solution for identifying medical instruments or devices, without the need of bulky arrays of spherical tracking markers, the present invention is specifically suitable for identifying smaller, hand-held medical devices or instruments.

In a further example, the inventive medical instrument or device may comprise
- at least one first group of markers is adapted to be recognized by at least one camera of a medical tracking system, particularly of an IR-tracking system, and/or
- at least one second group of markers is adapted to be recognized by a at least one camera of a medical microscope, which is in particular adapted to detect light within the visible range of light.

While each of the groups may contain the same information as to the instrument, at least one of the groups may also be utilized as a tracking marker arrangement which eventually allows the spatial position of a tracked instrument to be calculated.

In a third aspect, the invention is directed to a non-transitory computer-readable storage medium storing a computer program, which, when executed on at least one processor of at least one computer or loaded into the memory of at least one computer causes the at least one computer to perform a method that has been described further above.

In a fourth aspect, the invention is directed to at least one computer comprising the non-transitory computer readable program storage medium according to a third aspect. In a fifth aspect, the invention is directed to a medical tracking system comprising the above computer and a database stored on the computer on another computer that correspondingly links the codification data acquired from at least one image obtained from at least one camera, with the device data stored in the database. As already explained above, the codification data may contain information as to the properties of an instrument or device provided with the above described markers.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature and a feature of one embodiment which adds an additional function to another embodiment can for example be added to said other embodiment.

Definitions

In this section definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer, a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

Description of the Figures

In the following the invention is described with reference to the appended Figures which represent specific embodiments of the invention. The scope of the invention is however not limited to the specific features disclosed in the context of the Figures, wherein The medical instrument shown in FIG. 18 comprises an elongated shaft or body section 39 that reaches from a proximal instrument section or handle into a cavity within the body of a patient. For identifying the instrument properties as well as for tracking the instrument position within the three dimensional space, the instrument shaft 0.9 is provided at its proximal end with three ring-shaped retro-reflective IR markers 40, 41, and 42 which are adapted to be recognized by a medical tracking system 47 having a camera array with two IR cameras 44 and 45. The images provided by the cameras 44 and 45, showing the proximal tracking markers 40, 41, and 42 contain on the one hand, information as to the spatial position of the tracking markers 40, 41, and 42 and, on the other hand, information that helps to determine at least the length of shaft 39 between the tracking markers 40, 41, and 42 and the instrument tip within the patient's body. Further, the proximal markers 40, 41, and 42 are arranged along the same axis which is also the longitudinal axis of the instrument shaft 39. With the data described by the markers 40, 41, and 42, the orientation of the longitudinal axis of the instrument shaft 39, the length of the instrument shaft 39 extending from the markers 40, 41, and 42 and the spatial position of the instrument tip within the patient's body can be determined by a computer 46 which is provided with the information obtained by the tracking system 47. While the spatial position of the tracking markers 40, 41, and 42 and the orientation of the instrument shaft 39 can be directly taken from the camera images, the length of the instrument shaft 39 has to be looked up in the database 50 which is stored on the computer 46. Since the pattern formed by the tracking markers 40, 41, and 42 provides enough information to identify the instrument, the corresponding data set for this instrument is found in database 50.

Figure 18:
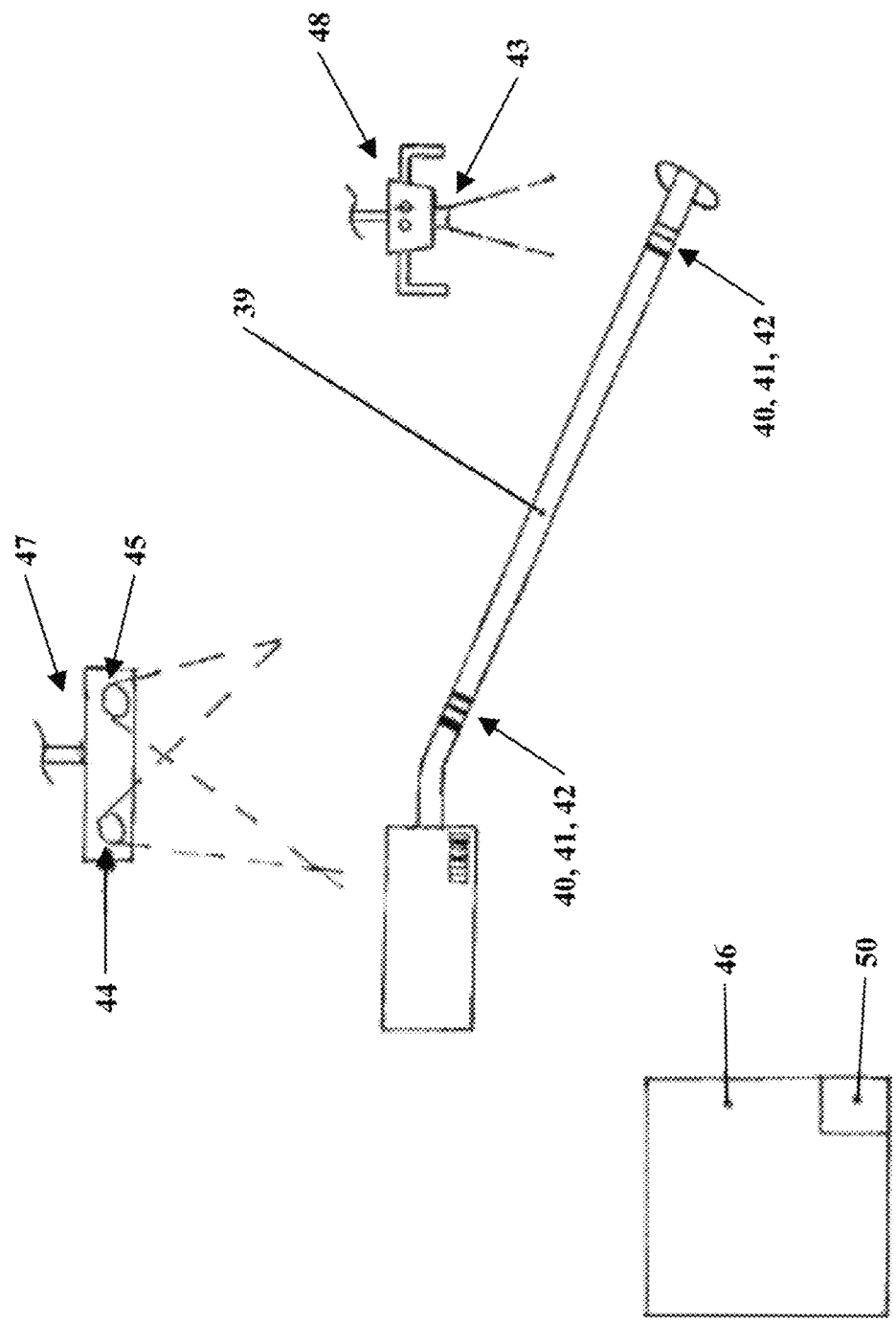
FIG. 18 shows an embodiment of the disclosed instrument/device and of the disclosed medical tracking system.

It further becomes apparent from FIG. 18 that the instrument is specifically adapted to be used in conjunction with a medical microscope 48 having a video camera 43. For that reason, the distal section of the instrument shaft 39 has a second group of markers 40, 41, and 42, by which the instrument can be identified, as well. In contrast to the proximal tracking markers 40, 41, and 42, the distal markers 40, 41, and 42 are adapted to be recognized by the video camera 43 of the microscope 48. Therefore, the distal markers 40, 41, and 42 may have a different color so that they even provide a color-coding. In case the proximal tracking markers 40, 41, and 42 are not within the field of view of the tracking system 47, the instrument can still be identified via the microscope 48, or vice versa.

In addition to the proximal tracking markers 40, 41, and 42 and the distal markers 40, 41, and 42 the proximal handle-section of the instrument is provided with a bar-code containing the same or a different amount of information about the instrument.

Figure 19:
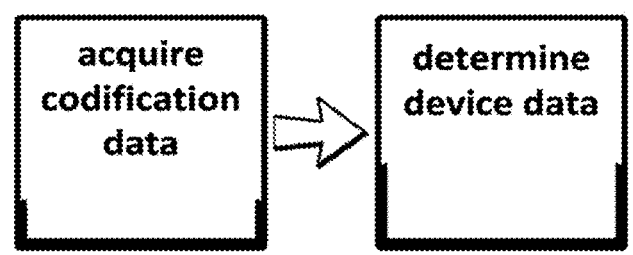
FIG. 19 shows a flow diagram comprising the basic steps of the disclosed method.

FIG. 19 shows the basic steps of the inventive identification method. Based on the codification data contained in the appearance and relative position of the markers 40, 41, and 42, which may be provided by the medical tracking system 47 or the medical microscope 48 shown in FIG. 18, device data describing the actual properties of a corresponding instrument or device is determined.

Specific Examples

A computer implemented medical method for identifying a medical device within a medical workspace, wherein the device has a body section 39 and is provided with at least two markers 40, 41, 42 adapted to be recognized by at least one optical camera 43, 44, 45, which run circumferentially around the body section 39, the method comprising executing, on a processor of a computer 46, the steps of:
  acquiring, at the processor, codification data describing at least one of the following
    the number of the markers 40, 41, 42,
    the color of at least one marker 40, 41, 42;
    the width of at least one marker 40, 41, 42; or
    the spacing between at least two markers 40, 41, 42;
  determining, by the processor and based on the codification data, device data describing properties of the device.
Wherein the codification data is acquired from at least one image obtained from said at least one camera 43, 44, 45, showing the at least two markers 40, 41, 42.
  Wherein the at least one camera 43, 44, 45 is assigned to
    a medical tracking system 47; or to
    a medical microscope 48.
  Wherein determining device data involves the step of acquiring, at the processor, the device data from a database 50, which is in particular stored on a computer 46 assigned to a medical tracking system that correspondingly links the codification data and the device data.
  Wherein the device data comprises information selected from the group consisting of:
    the device type;
    the device manufacturer,
    the material properties of the device; or
    the geometric properties of the device, particularly the geometric properties with respect to the markers 40, 41, 42.
  Further comprising the steps of:
    acquiring, at the processor, marker position data describing the spatial position of at least one of the markers 40, 41, 42;
    determining, by the processor and based on the marker position data and the device data describing the geometric properties of the device, device position data describing the spatial position of the device.
Wherein the marker position data is acquired from at least one image obtained from said at least one camera 43, 44, 45, showing the at least two markers 40, 41, 42.
Wherein the codification data and the marker position data is acquired from different cameras 43, 44, 45, particularly wherein
  the codification data is acquired from at least one camera 43 of a medical microscope 48; and
  the marker position data is acquired from at least one camera 44, 45 of a medical tracking system 47.
A medical device having an elongated body section 39 and comprising at least one group of at least two markers 40, 41, 42 which are adapted to be recognized by at least one optical camera 43, 44, 45, and which run circumferentially around the body section 39, wherein the at least two markers 43, 44, 45 of at least one of the groups form a pattern providing a predetermined code for the properties of the device.
  Wherein the code is based on at least one of the following:
    the number of the markers 43, 44, 45;
    the color of at least one marker 43, 44, 45;
    the width of at least one marker 43, 44, 45; or
    the spacing between at least two markers 43, 44, 45;
    and wherein the code is in particular a biunique code assigned to a single device. Wherein the medical device is a medical instrument, particularly a hand-held medical instrument.
Wherein
  at least one first group of markers 43, 44, 45 is adapted to be recognized by at least one camera 44, 45 of a medical tracking system 47, particularly of an IR-tracking system, and/or
  at least one second group of markers 43, 44, 45 is adapted to be recognized by a at least one camera 43 of a medical microscope 48, which is in particular adapted to detect light within the visible range of light.

A non-transitory, computer-readable storage medium storing a computer program which, when executed on a processor of a computer 46 or loaded into the memory of a computer 46, causes the computer 46 to perform a method.

A computer comprising the non-transitory, computer-readable program storage medium. A medical tracking system comprising the computer 46 and a database 50 stored on the computer 46 or another computer, that correspondingly links the codification data acquired from at least one image obtained from at least one camera 43, 44, 45, with the device data stored in the database 50, the codification data describing at least one of the following:
  the number of the markers 43, 44, 45;
  the color of at least one marker 43, 44, 45;
  the width of at least one marker 43, 44, 45; or
  the spacing between at least two markers 43, 44, 45;
  and the device data describing at least one of the following:
    the device type;
    the device manufacturer;
    the material properties of the device; or
    the geometric properties of the device, particularly the geometric properties with respect to the markers 43, 44, 45.

The invention claimed is:

1. A medical tracking method for tracking a spatial position of at least one medical instrument within a medical workspace that includes an anatomical structure of a patient, the method comprising:

acquiring, using a first camera targeted on the medical workspace, instrument position data describing a spatial position of the at least one medical instrument with respect to the first camera;

acquiring, using a second camera and at least one optical tracking marker that is adapted to be recognized by the second camera, camera position data describing a spatial position of the first camera with respect to the anatomical structure;

determining, using a computer and based on the instrument position data acquired using the first camera and the camera position data acquired using the second camera and the at least one optical tracking marker, tracking data describing the spatial position of the at least one medical instrument with respect to the anatomical structure;

tracking the spatial position of the at least one medical instrument within the medical workspace using the tracking data, wherein, the second camera is rigidly coupled to the first camera, and the at least one optical tracking marker is rigidly coupled to the anatomical structure, or the second camera is rigidly coupled to the anatomical structure, and the at least one optical tracking marker is rigidly coupled to the first camera.

2. The method according to claim 1, wherein the first camera is rigidly coupled to a medical microscope targeted on the medical workspace.

3. The method according to claim 1, wherein the first camera is freely movable relative to the anatomical structure.

4. The method according to claim 1, wherein the second camera is freely movable with respect to the anatomical structure and to the first camera, and wherein optical tracking markers are rigidly coupled to the anatomical structure and to the first camera.

5. The method according to claim 1, wherein acquiring camera position data involves changing a viewing direction of the second camera between the medical workspace and the tracking marker.

6. The method according to claim 1, further comprising:
acquiring, at the computer, registration data describing a spatial correspondence of a pre-acquired image dataset of the anatomical structure and the anatomical structure within the medical workspace;
wherein determining the tracking data is based on the registration data.

7. The method according to claim 6 wherein for acquiring the registration data the second camera is targeted on the medical workspace.

8. The method according to claim 1, wherein the at least one optical tracking marker comprises a two-dimensional optical pattern.

9. The method according to claim 6, wherein acquiring registration data involves at least one registration procedure selected from the list of:
a landmark registration using a tracked pointer instrument;
a landmark registration involving focusing a medical microscope on at least one predefined landmark of the anatomical structure;
a video registration using the medical microscope or a second video camera;
scanning the surface of the anatomical structure using a surface scanner.

10. A system for tracking a spatial position of at least one medical instrument within a medical workspace that includes an anatomical structure of a patient, the system comprising:
a first camera;
a second camera;
at least one optical tracking marker that is adapted to be recognized by the second camera; and
a computer operably associated with the first camera and the second camera, the computer configured to:
acquire, using the first camera targeted on the medical workspace, instrument position data describing a spatial position of the at least one medical instrument with respect to the first camera;
acquire, using the second camera and the at least one optical tracking marker, camera position data describing a spatial position of the first camera with respect to the anatomical structure;
determine, based on the instrument position data acquired using the first camera and the camera position data acquired using the second camera and the at least one optical tracking marker, tracking data describing the spatial position of the at least one medical instrument with respect to the anatomical structure; and
track the spatial position of the at least one medical instrument within the medical workspace using the tracking data,
wherein,
the second camera is rigidly coupled to the first camera, and the at least one optical tracking marker is rigidly coupled to the anatomical structure, or
the second camera is rigidly coupled to the anatomical structure, and the at least one optical tracking marker is rigidly coupled to the first camera.

11. A non-transitory computer-readable storage medium storing a computer program for tracking a spatial position of at least one medical instrument within a medical workspace that includes an anatomical structure of a patient which, when executed on a computer or loaded into the memory of a computer, causes the computer to:
acquire, using a first camera that is operably associated with the computer and is targeted on the medical workspace, instrument position data describing a spatial position of the at least one medical instrument with respect to the first camera;
acquire, using a second camera that is operably associated with the computer and at least one associated optical tracking marker, camera position data describing a spatial position of the first camera with respect to the anatomical structure;
determine, based on the instrument position data acquired using the first camera and the camera position data acquired using the second camera and the at least one associated optical tracking marker, tracking data describing the spatial position of the at least one medical instrument with respect to the anatomical structure; and
track the spatial position of the at least one medical instrument within the medical workspace using the tracking data,
wherein,
the second camera is rigidly coupled to the first camera, and the at least one optical tracking marker is rigidly coupled to the anatomical structure, or the second camera is rigidly coupled to the anatomical structure, and the at least one optical tracking marker is rigidly coupled to the first camera.

12. A computer comprising the non-transitory computer-readable storage medium according to claim 11.

13. The method according to claim 2, wherein the first camera is a microscope-integrated camera.

14. The method according to claim 5, wherein the viewing directions of the second camera between the medical workspace and the tracking marker are known.

15. The method according to claim 8, wherein the two-dimensional optical pattern is an orientation dependent optical pattern.

16. The system according to claim 10, wherein the first camera is rigidly coupled to a medical microscope targeted on the medical workspace.

17. The system according to claim 10, wherein the first camera is freely movable relative to the anatomical structure.

18. The system according to claim 10, wherein acquiring camera position data involves changing a viewing direction of the second camera between the medical workspace and the tracking marker.

19. The system according to claim 10, wherein the computer is further configured to:
    acquire registration data describing a spatial correspondence of a pre-acquired image dataset of the anatomical structure and the anatomical structure within the medical workspace;
    wherein determining the tracking data is based on the registration data.

* * * * *